United States Patent [19]

Vander Neut

[11] 4,306,808
[45] Dec. 22, 1981

[54] GLASS FLAW INSPECTION SYSTEM

[75] Inventor: Richard D. Vander Neut, Charlotte, N.C.

[73] Assignee: Ford Aerospace & Communications Corp., Detroit, Mich.

[21] Appl. No.: 103,682

[22] Filed: Dec. 14, 1979

[51] Int. Cl.³ ............................................. G01N 21/86
[52] U.S. Cl. .................... 356/239; 250/562; 250/572
[58] Field of Search ............. 356/239, 371, 430, 431; 250/562, 563, 572

[56] References Cited

U.S. PATENT DOCUMENTS

| 3,493,769 | 2/1970 | Revesz et al. | 356/431 X |
| 3,743,431 | 7/1973 | Cushing et al. | 356/239 |
| 3,792,930 | 2/1974 | Obenreder | 356/239 X |
| 3,866,038 | 2/1975 | Korth | 356/371 X |
| 3,925,049 | 12/1975 | Schwenninger | 356/239 X |

Primary Examiner—John K. Corbin
Assistant Examiner—Matthew W. Koren
Attorney, Agent, or Firm—Paul K. Godwin, Jr.; Clifford L. Sadler

[57] ABSTRACT

For inspecting a float glass ribbon for flaws an optical flaw detection system utilizing a laser beam which linescans the surface is provided. The laser beam is made incident to the glass ribbon at a high angle of incidence with respect to the normal. Deviation of the light transmitted through the glass ribbon is used as an indication of a defect. The invention is particularly useful for detecting "tin drip" type defects.

9 Claims, 5 Drawing Figures

GLASS FLAW INSPECTION SYSTEM

BACKGROUND OF THE INVENTION

1. Field of the Invention

The present invention is directed to the field of sheet material inspection and more specifically to the area of optical flaw detection in float-formed glass and the like.

2. Description of the Prior Art

Several prior art systems have been devised for the purpose of detecting optical transmission flaws which occur in glass at the time of its manufacture. Flaws, such as bubbles, dirt, viscous lumps and stones are generally detectable in prior art systems.

In commonly assigned U.S. Pat. No. 3,493,769 and U.S. Pat. No. 3,743,431, plate glass is scanned by a light beam which is point focused onto a surface of a glass sheet along a path orthogonal to the surface and is reflected back onto itself by a mirror on the opposite side of the glass. The '769 patent illustrates the use of a dark channel detection system whereby a perturbation or scattering of the incident and return beams will result in a detection. The '431 patent teaches the use of both a light and dark channel detection system whereby return light from unflawed material is detected in the light channel and perturbation or scattered light caused by a flaw is detected in the dark channel. The addition of the light channel is effective to increase the capability of the system in order to detect the occurrence of nonscattering occluding flaws.

SUMMARY OF THE INVENTION

In the production of float-formed glass, molten glass is poured onto a molten tin bath where it is formed as a flat ribbon. Several types of optical flaws may occur in the process which affect the quality of the product. One such flaw which affects high quality glass for mirrors is termed "tin drip". This flaw occurs when vaporized tin from the liquid float bath condenses and falls onto the surface of the flat ribbon. After annealing in a lehr, any tin drips which occur, appear as small cavities in the upper surface of the glass having sidewalls which slope downward from the surface at angles on the order of $\frac{1}{2}°$ to 2°. For most glass useage, tin drip flaws are inconsequential. However, in high quality mirror glass, tin drip flaws cannot be tolerated. The present invention is able to automatically detect such minor flaws as tin drips, as well as the more conventionally detected flaws and therefore represents a distinct improvement in this art. The present invention is uniquely suited for use in high volume, high quality, float-formed glass production facilities and provides 100% optical inspection of the output.

The ability of the present invention to detect localized flaws such as "tin drips" is due to the fact that the upper surface of the glass is scanned with a narrow collimated beam of electromagnetic radiation at an incident angle which is sufficiently large enough so that the emerging beam from the other side of the glass will be significantly diverted from its normally refracted path. In addition, light and dark channel detectors are employed along with appropriate circuitry to detect the occurrence of flaws, as well as distinguish them by type, size, location and frequency of occurrence.

It is therefore an object of the present invention to provide highly sensitive optical flaw detection systems for use in inspection of transparent ribbon or sheet material.

It is another object of the present invention to provide an optical flaw detection system ideally suited for use in conjunction with high volume production equipment of transparent sheet material.

It is a further object of the present invention to provide an optical flaw detection system that distinguishes between several types of detected flaws and produce a permanent record of said detections.

It is a still further object of the present invention to provide a highly sensitive optical flaw detection system utilizing a laser beam which is line-scanned onto the surface of the transparent sheet material at a high angle of incidence with respect to the normal.

BRIEF DESCRIPTION OF THE DRAWINGS

FIG. 5 is a plot of the change in emergence angle vs. the angle of incidence for various flaw slope angles.

TOTAL DESCRIPTION OF THE PREFERRED EMBODIMENT

Figure 1:
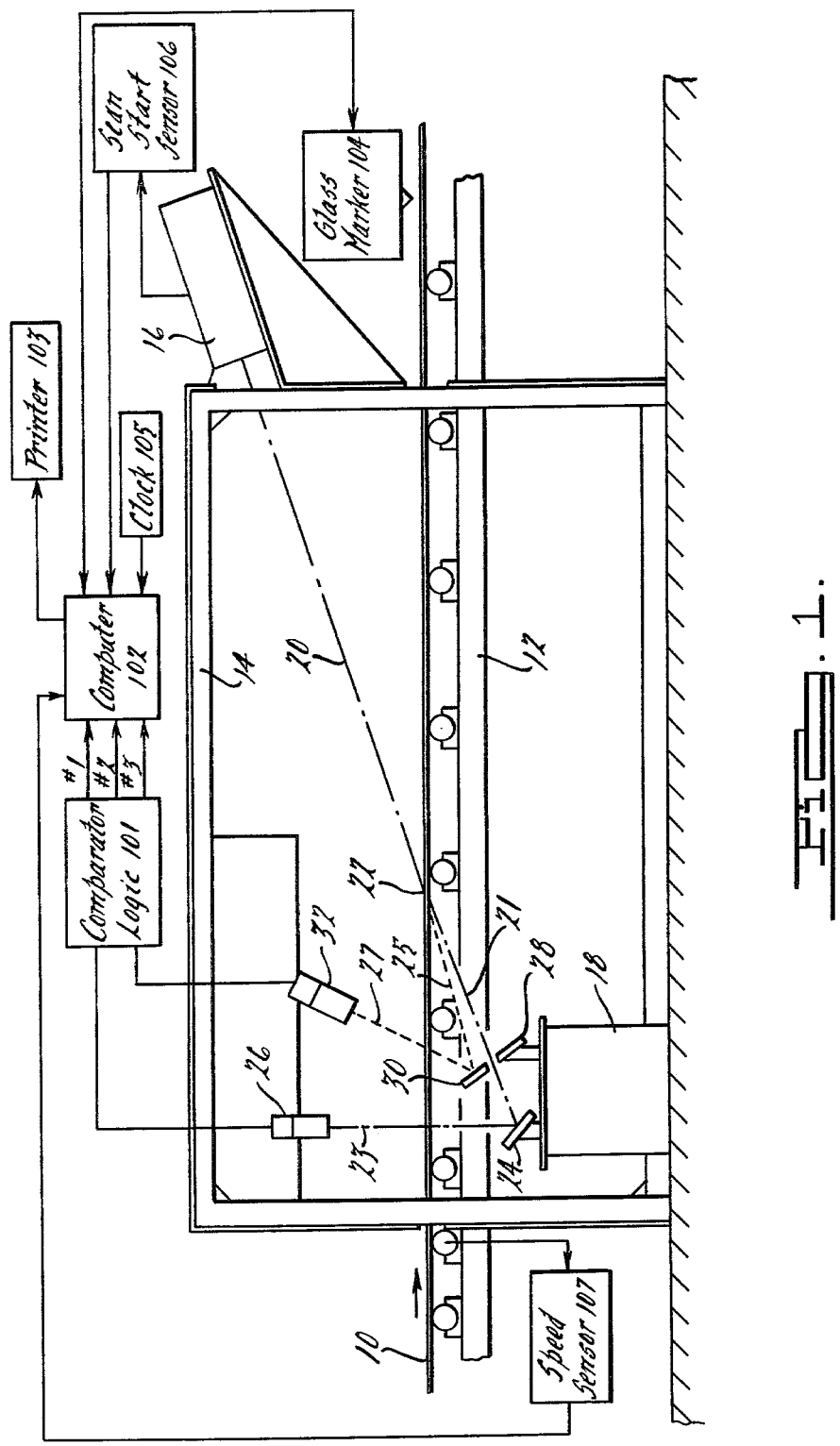
FIG. 1 is an overall view of the preferred embodiment of the present invention and includes a block diagram of the associated control system.

The preferred embodiment of the present invention is generally shown in FIG. 1 and employs an inspection station housing 14 which contains and supports the necessary inspection modules. The inspection station housing 14 is constructed so as to surround a portion of a glass transport conveyor 12 which, in a float-formed glass production facility may be located so as to inspect glass after it leaves an annealing lehr. A beam scanner 16 is supported on the housing 14 and incorporates a helium neon laser generator and multi-faceted flying spot scanner mirror (not shown) similar to that described in commonly assigned U.S. Patent No. 3,743,431, incorporated herein by reference. The scanner 16 outputs a collimated monochromatic light beam 20 incident onto the upper surface of the moving glass 10 at a point 22. The beam 20 is scanned in a direction orthogonal to the movement of the glass 10 so that inspection point 22, over a period of time, defines a line across the width of the glass.

A light channel detection means includes an elongated diffusing reflector 24 positioned transverse to the width of the glass 10 to receive the beam 21 as it emerges therefrom when its transmission therethrough is not disturbed by a flaw. According to Snell's law, the emerging beam path is parallel to the incident beam, but offset therefrom by a distance dependent upon the refractive index and thickness of the glass. The reflector 24 deflects the emerging beam along light channel path 21 in a direction defined by path 23 to a light channel detector assembly 26.

Figure 2:
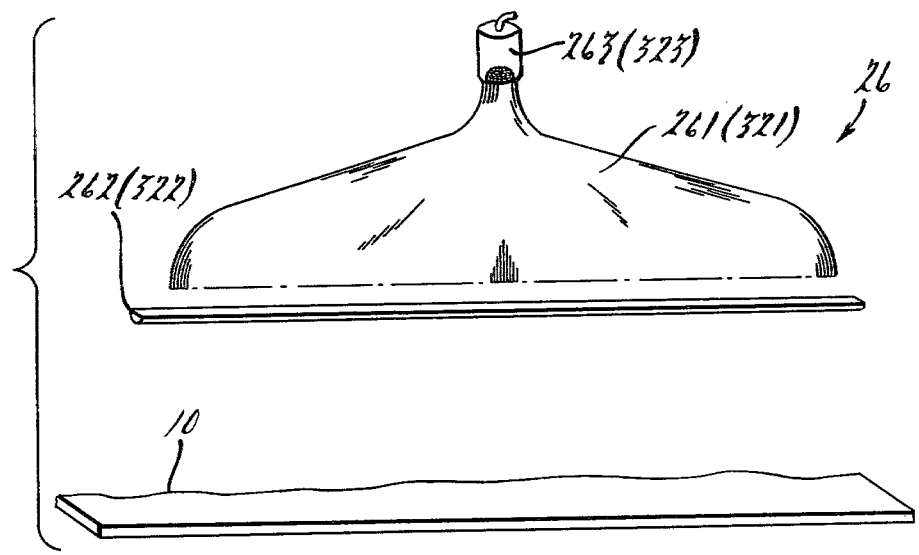
FIG. 2 is a detailed view of the line focus optical system employed in conjunction with light and dark channel detector assemblies.

The details of the light channel detector assembly 26 are shown in FIG. 2. The assembly 26 includes an elongated cylindrical lens 262, located above the moving glass 10 along a line generally parallel to the mirror 24. The cylindrical lens 262 images any light reflected by the reflector 24 onto its focal line. A fiber optic bundle 261 has one set of ends disposed along the focal line of the cylindrical lens 262 so as to receive any light reflected from the reflector 24 and imaged by the lens 262 onto the focal line. The other end of the fiber optic bundle 261 is disposed in a compact circular arrangement at the receiving end of a photodetector 263.

Figure 3:
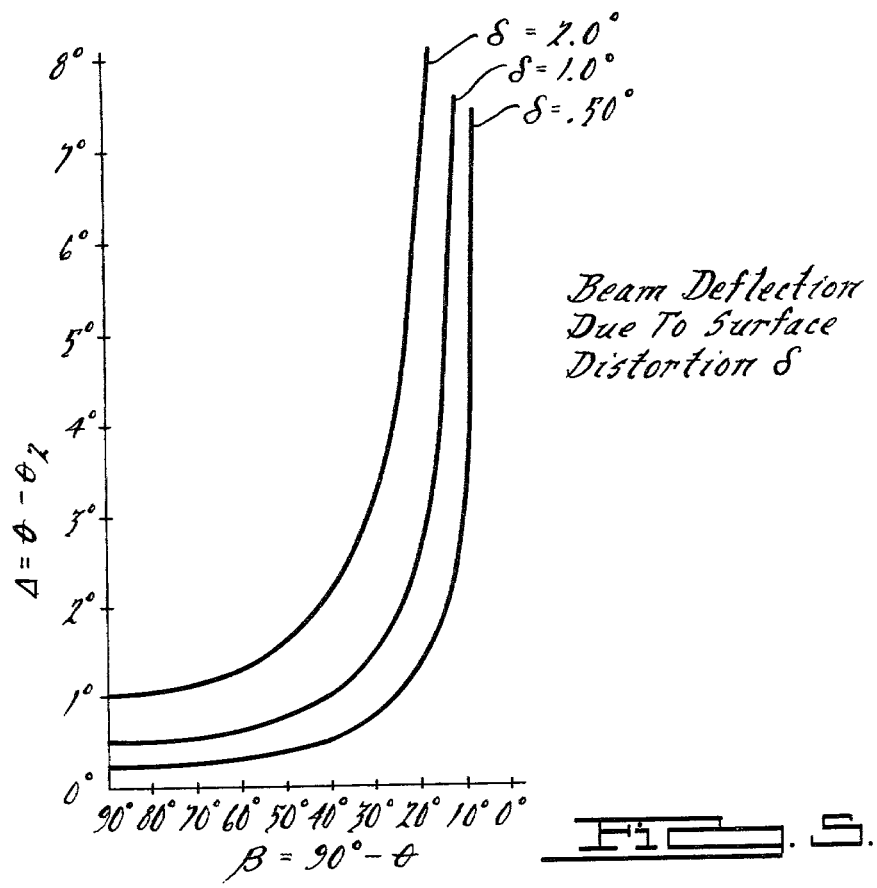
FIG. 3 is an optical ray drawing illustrating the entrance and exit paths of a light beam incident onto an unflawed portion of transparent sheet material.
Figure 3:
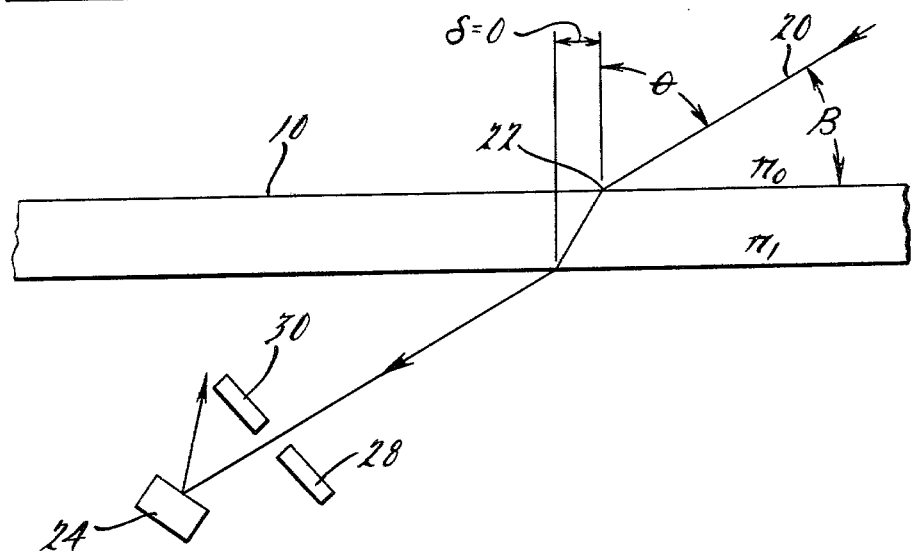

The refraction effects of unflawed glass on the incident beam 20 is shown in FIG. 3, wherein the entering beam 20 and the emerging beam along path 21 are parallel and offset a distance determined by the thickness of the glass 10.

Figure 4:
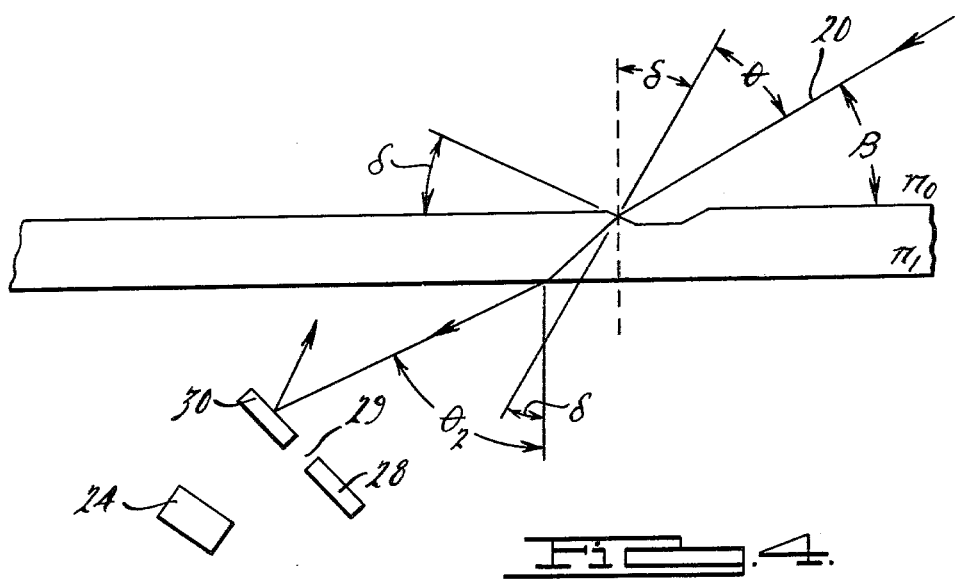
FIG. 4 is an exaggerated optical ray drawing illustrating the entrance and exit paths of a light beam incident onto a "tin drip" type flaw on a sheet of transparent material.

A low level tin drip type surface distortion is shown in FIG. 4 as an exaggerated depression in the surface of glass 10. It is exaggerated in order to clearly show the particular angular relationships discussed below and the effects as plotted in FIG. 5.

Tin drip localized defects normally cause depressions having sidewall slopes on the order of $\frac{1}{2}°$ or more. Therefore, the light and dark channel detection assembly locations as well as the incident beam angle must be calculated in order to effect a positive detection of such a minor defect. As shown in FIG. 4, the sidewall slope angle $\delta$ of the flaw causes the incident beam to exit at an angle $\phi_2$ with respect to the normal to the emerging surface. This emerging angle is different from that shown in the no defect state of FIG. 3, where the beam emerges at an angle $\phi$. The change in the emerging beam angle caused by the localized defect is calculated as $$\Delta = \phi - \phi_2 = \phi - [\sin^{-1}(n_1 \times \sin(\sin^{-1}(\sin/n_1)\phi + \delta))] - \delta.$$

Tin drip type defects having sidewall slope angles of 0.5°, 1° and 2° are plotted in FIG. 5 for various incident angles to illustrate the change in the emergent beam angle. From the plot of FIG. 5, it can be seen that where the incident angle is approximately 70° ($\beta = 20°$) even the relatively shallow tin drip defect of 0.5° results in an emerging beam being diverted by more than 1° from the light channel path. Therefore, a properly spaced mirror to the side of the light channel path 21 will reflect the diverted beam to a detector.

In order to detect the diverted beam, a "dark channel" detector assembly 32 is disposed so as to receive light reflected from either elongated diffusing reflectors 28 or 30 which are respectively disposed on either side of the light channel path 21. Therefore, a diverted beam, such as 25, will be reflected by reflector 30 along the path 27 to a dark channel detector assembly 26.

The dark channel detector assembly 32 is shown in FIG. 2 to include a cylindrical lens 322, a fiber optic bundle 321 and a photodetector 323. Cylindrical lens 322 is disposed so as to gather light reflected from either reflector 28 or 30 by including both reflectors in its field of view.

In the present embodiment, the reflectors are commonly mounted on a base 18 so as to reflect emerging light back through the glass 10 to corresponding light and dark channel detector assemblies. The detector assemblies 26 and 32 and the scanner 16 are all mounted above the transported glass 10 in order to provide for their protection in the event of glass breakage.

Additionally, it should be noted that while the inspection station housing 14 is substantially light-tight to prevent stray light from effecting the accuracy of the system, it may be necessary to include filters in each of the detector assemblies tuned to the monochromatic wavelength of the beam output by the scanner 16.

It should be further noted that although the present invention is highly sensitive in detecting the tin drip type flaws, it is also highly sensitive in detecting and distinguishing flaws which are classified as:
 (1) inclusions with transmission distortion;
 (2) inclusions without transmission distortion; and
 (3) transmission distortion only (including tin drips, bubbles, etc.)

Appropriate electronic circuitry monitors the system in order to classify, size, locate and record the detected flaws.

A comparator decoder logic circuit 101 is connected to both the light channel detector assembly 26 and the dark channel detector assembly 32 to compare the signal outputs from the photodetectors included in each assembly. When tin drip localized defects with low level distortion are illuminated by the light beam 20, the beam will be deflected so that a portion of it will strike a dark channel reflector and thereby cause a noticeable increase in light to the dark channel detector assembly 32. This simultaneously occurs along with a slight decrease in light intensity to the light channel detector assembly 26. The comparator logic circuit 101 classifies the detected tin drip type flaw as a #3 type and outputs an appropriate signal each time the scanned beam sweeps over that flaw.

Dirt flaws which do not effect the refractive properties of the glass will occlude or reduce light in the light channel and not cause light to be diverted to the dark channel. The comparator logic circuit 101 classifies such a flaw as a #2 type and outputs an appropriate signal each time the scanned beam sweeps over that flaw.

Similarly, stone inclusions which both occlude and effect refractive properties of the glass will both block light to the light channel and divert light to the dark channel. Such flaws are classified as #1 types and appropriate signals are output from the comparator logic circuit 101 when they are sensed. The length of time that such an indication is sensed for any one scan determines the width of the flaw. The number of successive times the flaw occurs at that location of the scan, correlated with the speed at which the glass is moving, determines the length of the flaw.

An appropriately programmed computer 102, receives inputs from the comparator logic circuit 101, a clocking circuit 105, a scan start sensor 106 and a transport speed sensor 107. The computer 102 utilizes the signal from the scan start sensor 106 to gate the clock pulses from the clocking circuit 105 to determine the transverse location of any sensed defect. The beginning of each scan is sensed by an auxiliary detector (not shown) within the scanner 16 and a gating signal is generated by the scan start sensor circuit 106. The computer 102 counts the number of gated clocking pulses between the start of a scan and the occurrence of a flaw, to determine the location of a flaw and the length of a single flaw detected in sequential scans when it is sensed at the same location in each scan, as opposed to detecting it as a separately occurring flaw in each scan.

The computer 102 utilizes the speed sensor signal 107 to determine the location of detected flaws along the length of the inspected glass 10 and to coordinate an edge-mark command signal to a glass marker 104 which is located down line from the actual inspection point. Such edge marking is useful for subsequent visual inspection.

A printer 103 is employed to provide a permanent record of the flaws detected in each glass ribbon 10 and is of conventional design.

It will be apparent that many modifications and variations may be effected without departing from the scope of the novel concept of this invention. Therefore, it is intended by the appended claims to cover all such modifications and variations which fall within the true spirit and scope of the invention.

What is claimed is:

1. A glass flaw inspection system comprising:
    means for transporting a sheet of glass past a predesignated inspection point;
    means for directing a beam of visible electromagnetic radiation to be incident on to a first surface of said glass at an angle greater than 45° at said inspection point;
    first means for detecting said incident radiation transmitted through said glass along a predetermined path;
    second means for detecting said incident radiation transmitted through said glass along paths diverting from said predetermined path.

2. An inspection system as in claim 1, wherein directing means includes means for generating a narrow collimated beam of visible electromagnetic radiation and means for repetitively scanning said beam in a line along said first surface of said glass.

3. An inspection system as in claim 2 wherein said transporting means includes a conveyor which provides linear movement of said glass in a direction generally orthogonal to said scan line.

4. An inspection system as in claims 2 or 3, wherein said first detecting means includes a first reflector positioned along said predetermined path to reflect radiation incident thereon and a photodetector positioned to receive said radiation reflected from said first reflector and produce a first electrical signal according to the intensity thereof.

5. An inspection system as in claim 4, wherein said second detecting means includes a second reflector positioned adjacent said predetermined path to reflect radiation incident thereon and a photodetector positioned to receive said radiation reflected from said second reflector and produce a second electrical signal according to the intensity thereof.

6. An inspection system as in claim 5, wherein said beam from said directing means is incident onto said glass at an angle within the range of 65° to 75° from the normal to said surface.

7. An inspection system as in claim 6, wherein said system further includes means for comparing said first and second electrical signals to determine the occurrences of optical flaws in said glass.

8. An inspection system as in claim 7, wherein said glass is transported in a generally horizontal plane; said directing means and said first and second photodetectors are positioned above said glass; and said first and second reflectors are positioned below said glass.

9. An inspection system as in claim 6, wherein said beam is incident onto said glass at an angle of approximately 70° from the normal to said surface.

* * * * *